United States Patent
Linker et al.

(10) Patent No.: US 6,573,219 B1
(45) Date of Patent: Jun. 3, 2003

(54) SUBSTITUTED HETEROCYCLYL-2H-CHROMENES

(75) Inventors: Karl-Heinz Linker, Leverkusen (DE); Roland Andree, Langenfeld (DE); Karl-Julius Reubke, Köln (DE); Otto Schallner, Monheim (DE); Mark Wilhelm Drewes, Langenfeld (DE); Peter Dahmen, Neuss (DE); Dieter Feucht, Monheim (DE); Rolf Pontzen, Leichlingen (DE)

(73) Assignee: Bayer Aktiengesellschaft, Leverkusan (DE)

( * ) Notice: Subject to any disclaimer, the term of this patent is extended or adjusted under 35 U.S.C. 154(b) by 0 days.

(21) Appl. No.: 10/049,189

(22) PCT Filed: Jul. 28, 2000

(86) PCT No.: PCT/EP00/07263

§ 371 (c)(1),
(2), (4) Date: Feb. 5, 2002

(87) PCT Pub. No.: WO01/10861

PCT Pub. Date: Feb. 15, 2001

(30) Foreign Application Priority Data

Aug. 10, 1999 (DE) .......................... 199 37 772

(51) Int. Cl.⁷ .................. A01N 43/54; A01N 43/56; A01N 43/653; A01N 43/707; C07D 405/04
(52) U.S. Cl. .................. 504/229; 504/230; 504/238; 504/243; 504/273; 504/280; 504/282; 504/285; 504/286; 544/310; 544/238; 544/215; 548/263.2; 548/263.4; 548/360.1; 548/364.4; 548/454
(58) Field of Search ............... 548/263.2, 263.4, 548/360.1, 364.4, 454; 544/310, 238, 15; 504/229, 230, 238, 243, 273, 280, 282, 285, 286

(56) References Cited

U.S. PATENT DOCUMENTS

| | | | |
|---|---|---|---|
| 5,378,681 A | 1/1995 | Schallner et al. | 504/273 |
| 5,476,946 A | 12/1995 | Linker et al. | 504/273 |
| 5,554,580 A | 9/1996 | Fischer et al. | 504/281 |
| 6,159,903 A | 12/2000 | Linker et al. | 504/229 |
| 6,162,765 A | 12/2000 | Linker et al. | 504/225 |

FOREIGN PATENT DOCUMENTS

| | | |
|---|---|---|
| CA | 2102750 | 5/1994 |
| CA | 2119673 | 9/1994 |
| DE | 38 10 706 | 10/1989 |
| EP | 400 403 | 12/1990 |
| WO | 97/08170 | 3/1997 |
| WO | 97/26248 | 7/1997 |
| WO | 97/40018 | 10/1997 |
| WO | 97/46535 | 12/1997 |
| WO | 99/31091 | 6/1999 |

OTHER PUBLICATIONS

*Chemical Abstracts, vol. 128, No. 4, Jan. 26, 1998, Columbus, Ohio, US; abstract No. 34781, Ito, Minoru et al: "Preparation of 2H-chromenes and their use as herbicides", XP002158256 in der Anmeldung erwähnt Zusammenfassung & JP 09 301973 A (Kumiai Chemical Industry Co., Ltd., Japan; Ihara Chemical Industry Co.,) Nov. 25, 1997.

*Primary Examiner*—Laura L. Stockton
(74) *Attorney, Agent, or Firm*—Richard E. L. Henderson; Raymond J. Harmuth

(57) ABSTRACT

The invention relates to novel substituted heterocyclyl-2H-chromenes of the general formula (I)

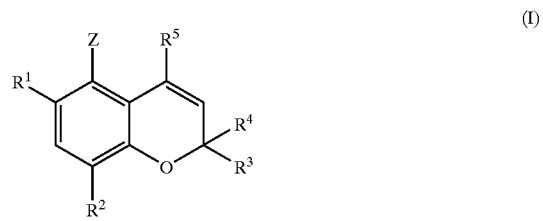

in which
$R^1, R^2, R^3, R^4, R_5$ Z are each as defined in the description, and to a process for their preparation and to their use as herbicides.

7 Claims, No Drawings

SUBSTITUTED HETEROCYCLYL-2H-CHROMENES

This application is a 371 of PCT/EP00/07263 filed Jul. 28, 2000.

The invention relates to novel substituted heterocyclyl-2H-chromenes, to a process for their preparation and to their use as herbicides.

It is already known that certain substituted heterocyclyl-2H-chromenes have herbicidal properties (cf. JP-A-09301973—cited in Chem. Abstracts 128:34781). However, these compounds have hitherto not attained any particular importance.

This invention, accordingly, provides the novel substituted heterocyclyl-2H-chromenes of the general formula (I)

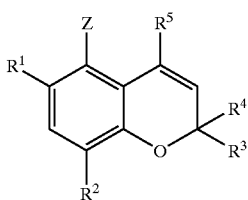

(I)

in which
$R^1$ represents hydrogen, cyano or halogen,
$R^2$ represents cyano, thiocarbamoyl, halogen or represents in each case substituted alkyl or alkoxy,
$R^3$ represents hydrogen, amino, nitro, formyl, carboxyl, cyano, carbamoyl, thiocarbamoyl, halogen, represents hydroxyiminoalkyl or represents in each case optionally substituted alkyl, alkoxy, alkylthio, alkylsulphinyl, alkylsulphonyl, alkylcarbonyl, alkoxycarbonyl, alkylcarbonylamino, alkoxyiminoalkyl, alkenyl, alkenyloxy, alkenylthio, alkinyl, alkinyloxy, alkinylthio, cycloalkyl, cycloalkylalkyl, cycloalkyloxycarbonyl, phenyl or benzyl,
$R^4$ represents hydrogen, halogen or optionally substituted alkyl,
$R^5$ represents hydrogen, halogen or optionally substituted alkyl, and
Z represents one of the heterocyclic groupings below

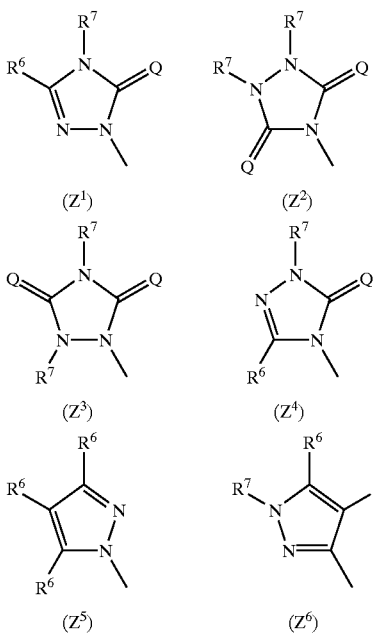

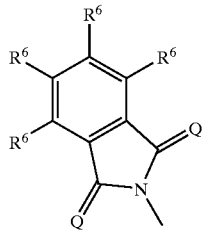

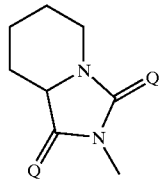

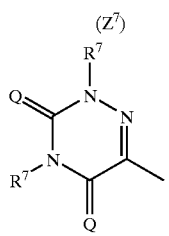

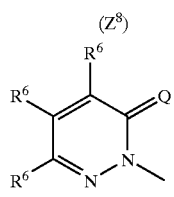

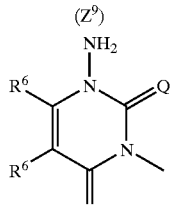

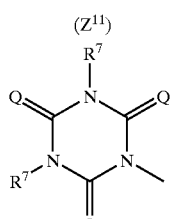

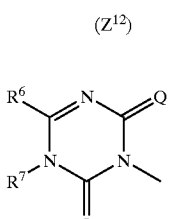

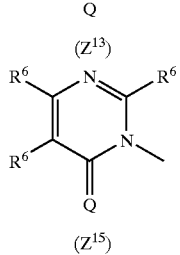

where
Q represents O (oxygen) or S (sulphur),
$R^6$ represents hydrogen, amino, nitro, cyano, carboxyl, carbamoyl, thiocarbamoyl, halogen, or represents in each case optionally substituted alkyl, alkoxy, alkylthio, alkylamino, alkoxycarbonyl, dialkylamino, alkenyl, alkenyloxy, alkenylthio, alkinyl, alkinyloxy, alkinylthio, cycloalkyl or cycloalkylalkyl, and
$R^7$ represents hydrogen, hydroxyl, amino, cyano, or represents in each case optionally substituted alkyl, alkoxy, alkoxycarbonyl, alkylamino, alkenyl, alkinyl, cycloalkyl, cycloalkylalkyl, phenyl or phenylalkyl,
where, if appropriate, two adjacent radicals—$R^6$ and $R^6$, $R^7$ and $R^7$ or $R^6$ and $R^7$—together represent alkanediyl or alkenediyl, each of which is optionally substituted and/or optionally interrupted at the beginning (and/or at the end) or within the hydrocarbon chain by O (oxygen), S (sulphur) or a grouping selected from the group consisting of —SO—, $SO_2$—, —NH— and —N(alkyl)—.

In the definitions, the hydrocarbon chains, such as alkyl or alkanediyl, are in each case straight-chain or branched—including in combination with heteroatoms, such as in alkoxy.

$R^1$ preferably represents hydrogen, cyano, fluorine, chlorine or bromine.

$R^2$ preferably represents cyano, thiocarbamoyl, fluorine, chlorine, bromine, or represents in each case optionally fluorine- and/or chlorine-substituted alkyl or alkoxy having in each case 1 to 4 carbon atoms.

$R^3$ preferably represents hydrogen, amino, nitro, formyl, carboxyl, cyano, carbamoyl, thiocarbamoyl, fluorine, chlorine, bromine, represents hydroxyiminoalkyl having up to 6 carbon atoms, represents in each case optionally cyano-, hydroxyl-, fluorine-, chlorine-, bromine-, $C_1$–$C_4$-alkoxy-, $C_1$–$C_4$-alkyl-thio-, $C_1$–$C_4$-alkylsulphinyl-, $C_1$–$C_4$-alkylsulphonyl-, $C_1$–$C_4$-alkylsulphonyloxy- or $C_1$–$C_4$-alkylcarbonyloxy-substituted alkyl, alkoxy, alkylthio, alkylsulphinyl or alkylsulphonyl having in each case up to 6 carbon atoms, represents in each case optionally cyano-, fluorine-, chlorine-, bromine- or $C_1$–$C_4$-alkoxy-substituted alkylcarbonyl, alkoxycarbonyl, alkylcarbonylamino or alkoxyiminoalkyl having in each case up to 6 carbon atoms, represents in each case optionally cyano-, fluorine-, chlorine- or bromine-substituted alkenyl, alkenyloxy, alkenylthio, alkinyl, alkinyloxy or alkinylthio having in each case up to 6 carbon atoms, represents in each case optionally cyano-, fluorine-, chlorine-, bromine- or $C_1$–$C_4$-alkyl-substituted cycloalkyl, cycloalkylalkyl or cycloalkyloxycarbonyl having in each case 3 to 6 carbon atoms in the cycloalkyl groups and optionally up to 4 carbon atoms in the alkyl moiety, or represents in each case optionally nitro-, cyano-, fluorine-, chlorine-, bromine-, $C_1$–$C_4$-alkyl- or $C_1$–$C_4$-alkoxy-substituted phenyl or benzyl.

$R^4$ preferably represents hydrogen, fluorine, chlorine, bromine, or represents optionally cyano-, fluorine-, chlorine- or $C_1$–$C_4$-alkoxy-substituted alkyl having 1 to 6 carbon atoms.

$R^5$ preferably represents hydrogen, fluorine, chlorine, bromine, or represents optionally cyano-, fluorine-, chlorine- or $C_1$–$C_4$-alkoxy-substituted alkyl having 1 to 6 carbon atoms.

Z preferably represents one of the heterocyclic groupings below

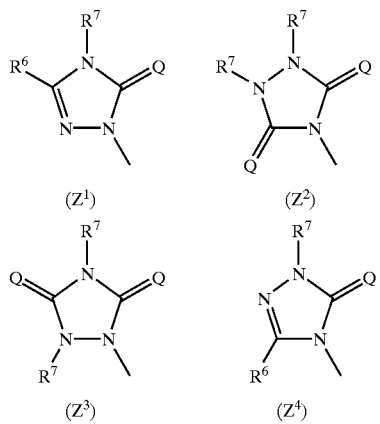

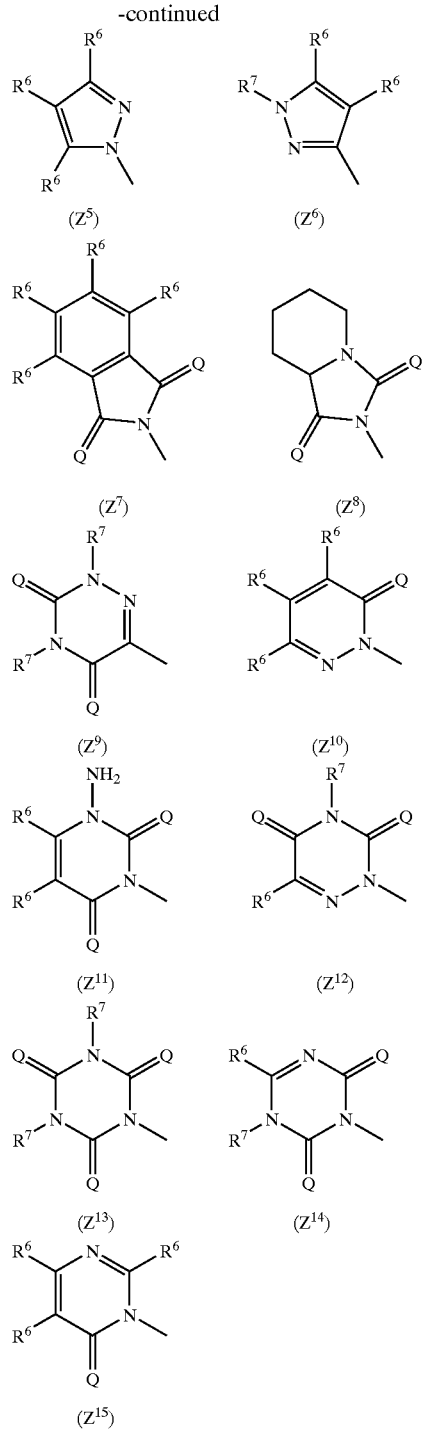

where

Q preferably represents O (oxygen) or S (sulphur).

$R^6$ preferably represents hydrogen, amino, nitro, cyano, carboxyl, carbamoyl, thiocarbamoyl, halogen, represents in each case optionally cyano-, halogen- or $C_1$–$C_4$-alkoxy-substituted alkyl, alkoxy, alkylthio, alkylamino or alkoxycarbonyl having in each case up to 6 carbon atoms, represents dialkylamino having in each case up to 4 carbon atoms in the alkyl groups, represents in each case optionally cyano- or halogen-substituted alkenyl, alkinyl, alkenyloxy, alkinyloxy, alkenylthio, alkinylthio having in each case up to 6 carbon atoms, or represents in each case optionally cyano-, halogen- or $C_1$–$C_4$-alkyl-substituted cycloalkyl or cycloalkylalkyl having in each case 3 to 6 carbon atoms in the cycloalkyl groups and optionally up to 4 carbon atoms in the alkyl moiety.

$R^7$ preferably represents hydrogen, hydroxyl, amino, cyano, represents in each case optionally cyano-, halogen- or $C_1$–$C_4$-alkoxy-substituted alkyl, alkoxy, alkoxycarbonyl or alkylamino having in each case up to 6 carbon atoms, represents in each case optionally cyano- or halogen-substituted alkenyl or alkinyl having in each case up to 6 carbon atoms, represents in each case optionally cyano-, halogen- or $C_1$–$C_4$-alkyl-substituted cycloalkyl or cycloalkylalkyl having in each case 3 to 6 carbon atoms in the cycloalkyl groups and optionally up to 4 carbon atoms in the alkyl moiety, or represents in each case optionally nitro-, cyano-, halogen-, $C_1$–$C_4$-alkyl- or $C_1$–$C_4$-alkoxy-substituted phenyl, benzyl or phenylethyl.

Two adjacent radicals—$R^6$ and $R^6$, $R^7$ and $R^7$ or $R^6$ and $R^7$—preferably together represent alkanediyl or alkenediyl having in each case up to 5 carbon atoms and being in each case optionally substituted by halogen and/or interrupted at the beginning (and/or at the end) or within the hydrocarbon chain by O (oxygen), S (sulphur) or a grouping selected from the group consisting of —SO—, —$SO_2$—, —NH— and —N($C_1$–$C_4$-alkyl)—.

$R^1$ particularly preferably represents hydrogen, fluorine or chlorine.

$R^2$ particularly preferably represents cyano, thiocarbamoyl, fluorine, chlorine, bromine, trifluoromethyl, difluoromethoxy or trifluoromethoxy.

$R^3$ particularly preferably represents hydrogen, amino, nitro, formyl, carboxyl, cyano, carbamoyl, thiocarbamoyl, fluorine, chlorine, bromine, represents hydroxyiminomethyl, hydroxyiminoethyl or hydroxyiminopropyl, represents in each case optionally cyano-, hydroxyl-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl or ethylsulphonyl, represents in each case optionally cyano-, fluorine-, chlorine-, methoxy- or ethoxy-substituted acetyl, propionyl, n-or i-butyroyl, methoxycarbonyl, ethoxycarbonyl, n- or i-propoxycarbonyl, acetylamino, propionylamino, n- or i-butyroylamino, methoxyiminomethyl, ethoxyiminomethyl, methoxyiminoethyl or ethoxyiminoethyl, represents in each case optionally cyano-, fluorine- or chlorine-substituted propenyl, butenyl, propenyloxy, butenyloxy, propenylthio, butenylthio, propinyl, butinyl, propinyloxy, butinyloxy, propinylthio or butinylthio, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl, cyclohexylmethyl, cyclopropyloxycarbonyl, cyclobutyloxycarbonyl, cyclopentyloxycarbonyl or cyclohexyloxycarbonyl, or represents in each case optionally nitro-, cyano-, fluorine-, chlorine-, bromine-, methyl- or methoxy-substituted phenyl or benzyl.

$R^4$ particularly preferably represents hydrogen, fluorine, chlorine, bromine, or represents in each case optionally cyano-, fluorine-, chlorine-, methoxy- or ethoxy-substituted methyl, ethyl, n- or i-propyl.

$R^5$ particularly preferably represents hydrogen, fluorine, chlorine, bromine, or represents in each case optionally cyano-, fluorine-, chlorine-, methoxy- or ethoxy-substituted methyl, ethyl, n- or i-propyl.

Z particularly preferably represents one of the heterocyclic groupings below

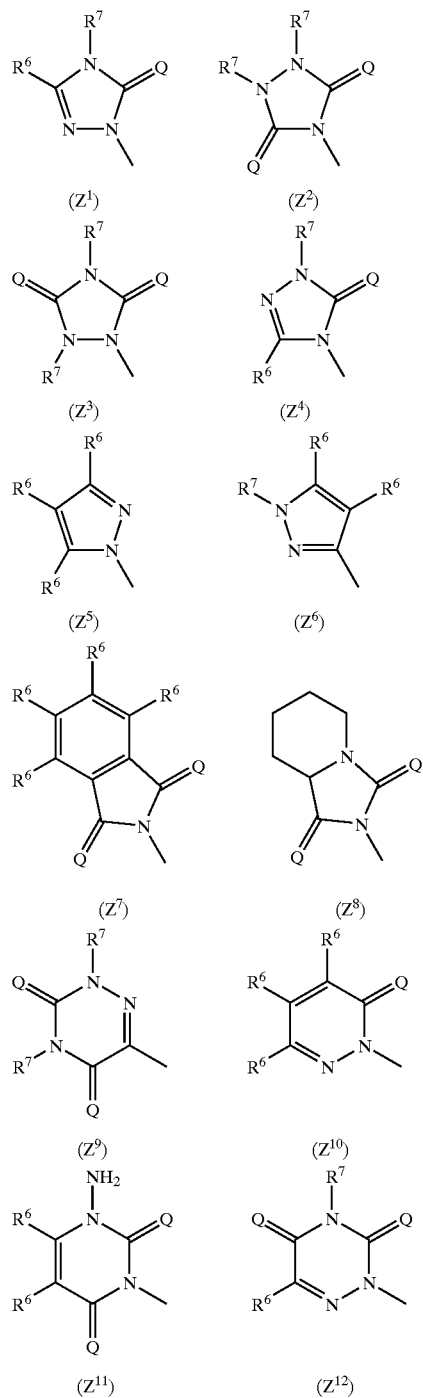

-continued

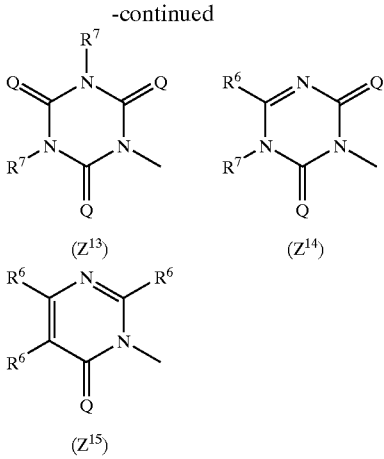

where
Q particularly preferably represents O (oxygen) or S (sulphur).

$R^6$ particularly preferably represents hydrogen, amino, nitro, cyano, carboxyl, carbamoyl, thiocarbamoyl, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino, methoxycarbonyl, ethoxycarbonyl, n- or i-propoxycarbonyl, n-, i-, s- or t-butoxycarbonyl, represents dimethylamino or diethylamino, represents in each case optionally cyano-, fluorine-, chlorine- or bromine-substituted propenyl, butenyl, propinyl, butinyl, propenyloxy, butenyloxy, propinyloxy, butinyloxy, propenylthio, butenylthio, propinylthio or butinylthio, or represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl.

$R^7$ particularly preferably represents hydrogen, hydroxyl, amino, cyano, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methoxycarbonyl, ethoxycarbonyl, n- or i-propoxycarbonyl, n-, i-, s- or t-butoxycarbonyl, methylamino, ethylamino, n- or i-propylamino, n-, i-, s- or t-butylamino, represents in each case optionally cyano-, fluorine- or chlorine-substituted propenyl, butenyl, propinyl or butinyl, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl- or methoxy-substituted phenyl or benzyl.

Two adjacent radicals—$R^6$ and $R^6$, $R^7$ and $R^7$ or $R^6$ and $R^7$—particularly preferably together represent propane-1,3-diyl(trimethylene), butane-1,4-diylo(tetramethylene), pentane-1,5-diyl(pentamethylene), propene-1,3-diyl, but-1-ene-1,4-diyl or but-2-ene-1,4-diyl, each of which is optionally substituted by fluorine or chlorine and/or optionally interrupted at the beginning (and/or at the end) or within the hydrocarbon chain by O (oxygen), S (sulphur) or a grouping selected from the group consisting of —SO—, —SO$_2$—, —NH— and —N(methyl)—.

$R^1$ very particularly preferably represents hydrogen or fluorine.

$R^2$ very particularly preferably represents cyano, thiocarbamoyl, chlorine or bromine.

$R^3$ very particularly preferably represents hydrogen, carboxyl, cyano, carbamoyl, thiocarbamoyl, fluorine, chlorine, bromine, represents in each case optionally fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl or ethylsulphonyl, represents in each case optionally cyano-, fluorine-, chlorine-, methoxy- or ethoxy-substituted methoxycarbonyl, ethoxycarbonyl, n- or i-propoxycarbonyl.

$R^4$ very particularly preferably represents hydrogen, fluorine, chlorine, bromine, or represents in each case optionally fluorine-, chlorine-, methoxy- or ethoxy-substituted methyl, ethyl, n- or i-propyl.

$R^5$ very particularly preferably represents hydrogen, fluorine, chlorine, bromine, or represents in each case optionally fluorine-, chlorine-, methoxy- or ethoxy-substituted methyl, ethyl, n- or i-propyl.

Z very particularly preferably represents one of the heterocyclic groupings below

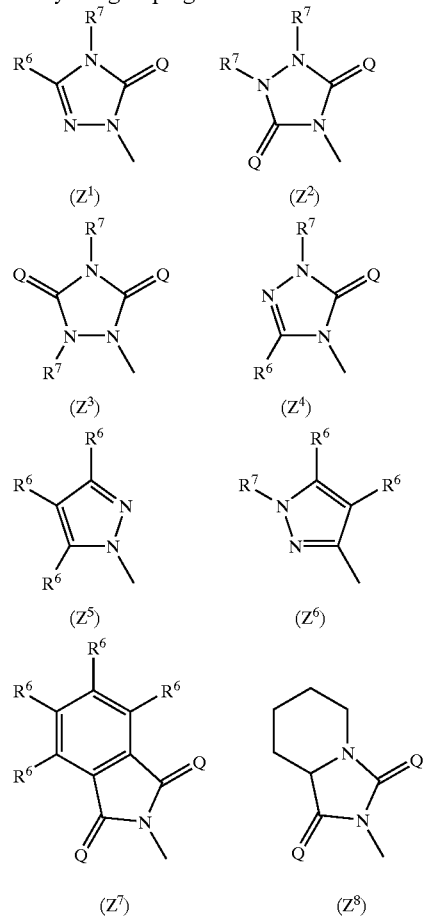

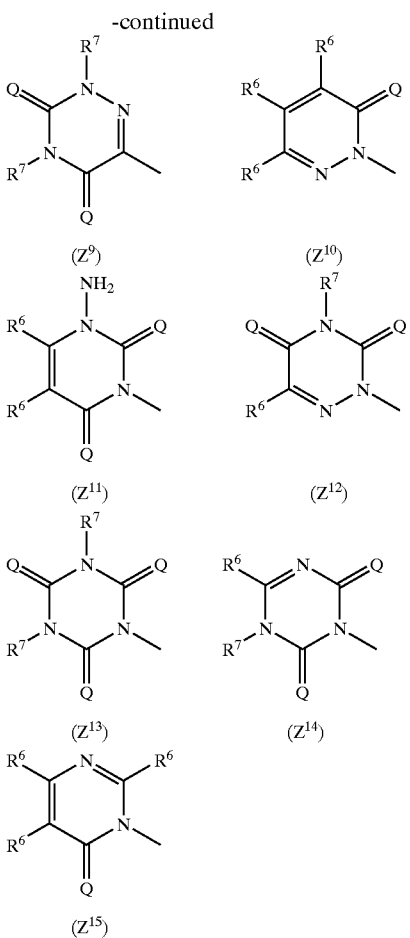

where
Q very particularly preferably represents O (oxygen) or S (sulphur).

$R^6$ very particularly preferably represents hydrogen, fluorine, chlorine, bromine, represents in each case optionally fluorine-, chlorine-, methoxy- or ethoxy-substituted methyl, ethyl, n- or i-propyl, methoxy, ethoxy, n- or i-propoxy, methylamimo, ethylamino, n- or i-propylamino, represents dimethylamino, represents in each case optionally cyano-, fluorine-, chlorine- or bromine-substituted propenyl, butenyl, propinyl, butinyl, propenyloxy, butenyloxy, propinyloxy, butinyloxy, propenylthio, butenylthio, propinylthio or butinylthio.

$R^7$ very particularly preferably represents hydrogen, represents amino, represents in each case optionally fluorine-, chlorine-, methoxy- or ethoxy-substituted methyl, ethyl, n- or i-propyl, or represents in each case optionally cyano-, fluorine- or chlorine-substituted propenyl, butenyl, propinyl or butinyl.

Two adjacent radicals—$R^6$ and $R^6$, $R^7$ and $R^7$ or $R^6$ and $R^7$—very particularly preferably together represent propane-1,3-diyl(trimethylene), butane-1,4-diyl (tetramethylene), pentane-1,5-diyl(pentamethylene), propene-1,3-diyl, but-1-ene-1,4-diyl or but-2-ene-1,4-diyl, each of which is optionally substituted by fluorine or chlorine and/or optionally interrupted at the beginning (and/or at the end) or within the hydrocarbon chain by O (oxygen), S (sulphur) or a grouping selected from the group consisting of —SO—, —SO$_2$—, —NH— and —N(methyl)—.

$R^1$ most preferably represents fluorine.
$R^2$ most preferably represents cyano, thiocarbamoyl or chlorine.
$R^3$ most preferably represents hydrogen or methyl.
$R^4$ and $R^5$ each most preferably represent hydrogen.

The individual radicals $R^6$ and $R^7$—if more than one of them are attached to the same heterocyclic grouping—can have identical or different meanings within the scope of the definitions mentioned above as being preferred, particularly preferred or very particularly preferred.

The general or preferred radical definitions mentioned above apply both to the end products of the formula (I) and, correspondingly, to the starting materials or intermediates required in each case for the preparation. These radical definitions can be combined with one another as desired, i.e. including combinations between the given preferred ranges.

Preference according to the invention is given to those compounds of the formula (I) which contain a combination of the meanings listed above as being preferred.

Particular preference according to the invention is given to those compounds of the formula (I) which contain a combination of the meanings listed above as being particularly preferred.

Very particular preference according to the invention is given to those compounds of the formula (I) which contain a combination of the meanings listed above as being very particularly preferred.

Most preference according to the invention is given to those compounds of the formula (I) in which one radical has the meaning listed above as being most preferred.

A very particularly preferred group are those compounds of the formula (I) in which
$R^1$, $R^2$, $R^3$, $R^4$ and $R^5$ each have the meanings mentioned above as being very particularly preferred and
Z represents the heterocyclic grouping below

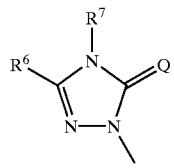

in which
Q, $R^6$ and $R^7$ each have the meaning mentioned above as being very particularly preferred.

A further very particularly preferred group are those compounds of the formula (I) in which
$R^1$, $R^2$, $R^3$, $R^4$ and $R^5$ each have the meanings mentioned above as being very particularly preferred and
Z represents the heterocyclic grouping below

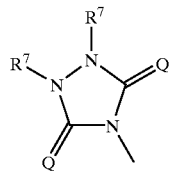

in which
Q and $R^7$ each have the meaning mentioned above as being very particularly preferred.

A further very particularly preferred group are those compounds of the formula (I) in which
R¹, R², R³, R⁴ and R⁵ each have the meanings mentioned above as being very particularly preferred and
Z represents the heterocyclic grouping below (Z⁵)

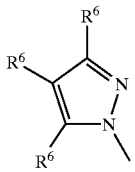

in which
R⁶ has the meaning mentioned above as being very particularly preferred.

A further very particularly preferred group are those compounds of the formula (I) in which
R¹, R², R³, R⁴ and R⁵ each have the meanings mentioned above as being very particularly preferred and
Z represents the heterocyclic grouping below (Z⁶)

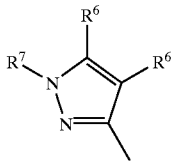

in which R⁶ and R⁷ each have the meaning mentioned above as being very particularly preferred.

A further very particularly preferred group are those compounds of the formula (I) in which
R¹, R², R³, R⁴ and R⁵ each have the meanings mentioned above as being very particularly preferred and
Z represents the heterocyclic grouping below (Z⁷)

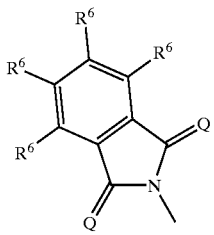

in which
Q and R⁶ each have the meaning mentioned above as being very particularly preferred.

A further very particularly preferred group are those compounds of the formula (I) in which
R¹, R², R³, R⁴ and R⁵ each have the meanings mentioned above as being very particularly preferred and
Z represents the heterocyclic grouping below (Z¹⁰)

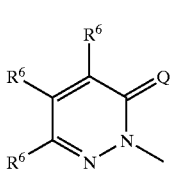

in which
Q and R each have the meaning mentioned above as being very particularly preferred.

A further very particularly preferred group are those compounds of the formula (I) in which
R¹, R², R³, R⁴ and R⁵ each have the meanings mentioned above as being very particularly preferred and
Z represents the heterocyclic grouping below (Z¹¹)

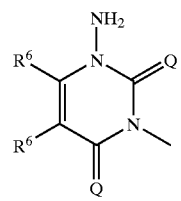

in which
Q and R⁶ each have the meaning mentioned above as being very particularly preferred.

A further very particularly preferred group are those compounds of the formula (I) in which
R¹, R², R³, R⁴ and R⁵ each have the meanings mentioned above as being very particularly preferred and
Z represents the heterocyclic grouping below (Z¹²)

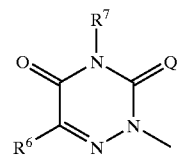

in which
Q, R⁶ and R⁷ each have the meaning mentioned above as being very particularly preferred.

A further very particularly preferred group are those compounds of the formula (I) in which
R¹, R², R³, R⁴ and R⁵ each have the meanings mentioned above as being very particularly preferred and
Z represents the heterocyclic grouping below (Z¹³)

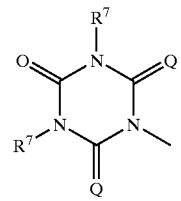

in which
Q and R⁷ each have the meanings mentioned above as being very particularly preferred.

The novel substituted heterocyclyl-2H-chromenes of the general formula (I) have interesting biological properties. In particular, they have strong herbicidal activity. The novel substituted heterocyclyl-2H-chromenes of the general formula (I) are obtained when 3-alkinyloxy-phenylheterocycles of the general formula (II)

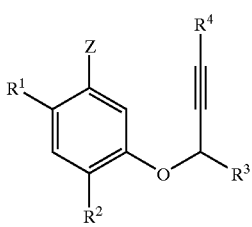

in which

R¹, R², R³, R⁴ and Z are each as defined above are pyrolysed in the presence of basic nitrogen compounds.

Using, for example, 4-(3-chloro-4-methyl-5-oxo-4,5-dihydro-1H-1,2,4-triazol-1-yl)-5-fluoro-2-[(1-methyl-2-propinyl)-oxy]-benzonitrile as starting material, the course of the reaction in the process according to the invention can be illustrated by the following formula scheme:

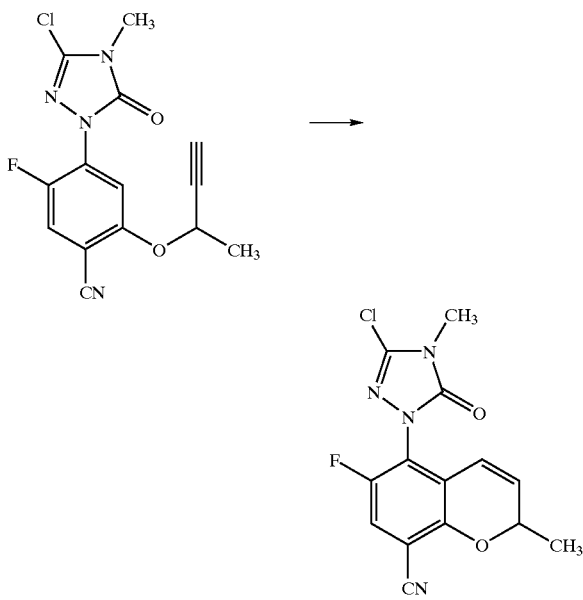

The formula (II) provides a general definition of the 3-alkinyloxy-phenylheterocycles to be used as starting materials in the process according to the invention for preparing compounds of the general formula (I). In the general formula (II), R¹, R², R³, R⁴ and Z each preferably or in particular have those meanings which have already been mentioned above, in connection with the description of the compounds of the general formula (I) according to the invention, as being preferred or as being particularly preferred for R¹, R², R³, R⁴ and Z.

The starting materials of the general formula (II) are known and/or can be prepared by processes known per se (cf. EP-A-370332, EP-A-597360, EP-A-599135, EP-A-610733, EP-A-617026, WO-A-96/18618, WO-A-97/30980, WO-A-97/26248, WO-A-97/40018, WO-A-97/46535, Preparation Examples).

The process for preparing compounds of the general formula (I) is carried out using basic organic nitrogen compounds. These preferably include triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-diethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN) and 1,8-diazabicyclo-[5.4.0]-undec-7-ene (DBU).

The process for preparing compounds of the general formula (I) is, if appropriate, carried out using metal fluorides. These preferably include lithium fluoride, sodium fluoride, potassium fluoride, rubidium fluoride, caesium fluoride, magnesium fluoride, calcium fluoride, barium fluoride and aluminium fluoride.

When carrying out the process according to the invention, the reaction temperatures can be varied within a relatively wide range. In general, the process is carried out at temperatures between 150° C. and 250° C., preferably between 180° C. and 220° C.

The process according to the invention is generally carried out under atmospheric pressure. However, it is also possible to carry out the process according to the invention under elevated or reduced pressure—in general between 0.1 bar and 10 bar. When carrying out the process according to the invention, the reaction components are generally mixed at room temperature, and the reaction mixture is generally stirred at the required temperature for one or more hours. Work-up is carried out by customary methods (cf the Preparation Examples).

The active compounds according to the invention can be used as defoliants, desiccants, haulm killers and, especially, as weed killers. By weeds in the broadest sense are to be understood all plants which grow in locations where they are undesired. Whether the substances according to the invention act as total or selective herbicides depends essentially on the amount used. The active compounds according to the invention can be used, for example, in connection with the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compounds according to the invention is in no way restricted to these genera, but also extends in the same manner to other plants.

Depending on the concentration, the active compounds according to the invention are suitable for total weed control, for example on industrial terrain and railway tracks and on paths and areas with or without tree growth. Equally, the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The active compounds of the formula (I) according to the invention have strong herbicidal activity and a broad activity spectrum when used on the soil and on aboveground parts of plants. To a certain extent, they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be used for controlling animal pests and fungal or bacterial plant diseases. If appropriate, they can also be employed as intermediates or precursors for the synthesis of other active compounds.

According to the invention, it is possible to treat all plants and parts of plants. By plants are to be understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, shoot-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

The active compounds according to the invention, as such or in their formulations, can also be employed in a mixture with known herbicides and/or with substances which improve crop plant safety ("safeners") for controlling weeds, finished formulations or tank mixes being possible. Also possible are mixtures with herbicides comprising one or more known herbicides and a safener.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole; caloxydim, carbetamide, carfentrazone(-ethyl), chlomethoxyfen, chloramben, chloridazon, chlorimuron(-ethyl), chlornitrofen, chlorsulfuron, chlorotoluron, cinidon (-ethyl), cinmethylin, cinosulfuron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop (-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron (-methyl), ethofumesate, ethoxyfen, ethoxysulfuron, etobenzanid, fenoxaprop-(-P-ethyl), fentrazamide, flamprop (-isopropyl), flamprop(-isopropyl-L), flamprop(-methyl), flazasulfuron, florasulam, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-P-methyl), hexazinone, imazamethabenz-(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac-(-methyl), pyrithiobac(-sodium), quinchlorac, quinmerac, quinoclamine, quizalofop (-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

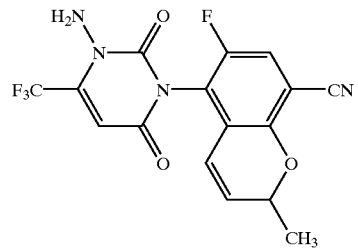

A mixture of 0.5 g (1.3 mmol) of 3-[2-fluoro-4-cyano-5-(but-1-in-3-yl-oxy)-phenyl]-1-amino-6-trifluoromethyl-(1H,3H)-pyrimidine-2,4-dione and 15 ml of N,N-diethylaniline is stirred at 210° C. for 2 hours and, after cooling, mixed with water. The precipitated product is isolated by filtration with suction. The filtrate is shaken with ethyl acetate and the organic phase is dried over sodium sulphate and filtered. The filtrate is concentrated under water pump vacuum. The residue and the solid which was isolated by filtration with suction are combined and purified by silica gel column chromatography using cyclohexane/ethyl acetate (vol.: 3:1).

This gives 0.20 g (40% of theory) of 1-amino-6-trifluoromethyl-3-(6-fluoro-8-cyano-2-methyl-chromen-3-yl)-(1H,3H)-pyrimidine-2,4-dione.
$^1$H-NMR (DMSO-$d_6$): 7.80; 7.83 (d 1H).

Example 2

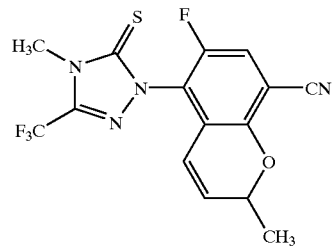

A mixture of 0.85 g (2.3 mmol) of 1-[2-fluoro-4-cyano-5-(but-1-in-3-yl-oxy)-phenyl]-4-methyl-3-trifluoromethyl-2,4-dihydro-3H-1,2,4-triazole-5-thione and 12 ml of N,N-diethyl-aniline is stirred at 210° C. for 2 hours and, after cooling, poured into ice-water and acidified (pH 2) using conc. hydrochloric acid. The precipitated product is isolated by filtration with suction, washed with water and dried.

This gives 0.84 g (98% of theory) of 1-(8-cyano-6-fluoro-2-methyl-chromen-3-yl)-4-methyl-3-trifluoromethyl-1,2,4 (1H,4H)-triazole-5-thione of melting point 144° C. (logP: 3.37).

Analogously to Examples 1 and 2, and in accordance with the general description of the general description of the preparation process according to the invention, it is also possible to prepare, for example, the compounds of the general formula (I) listed in Table 1 below.

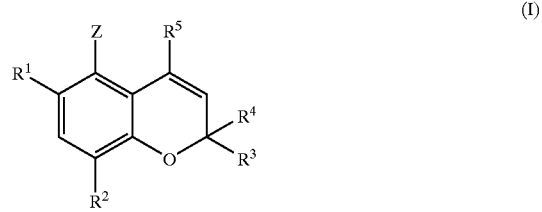

TABLE 1

Examples of the compounds of the formla (I)

| Ex. No. | Z | $R^1$ | $R^2$ | $R^3$ | $R^4$ | $R^8$ | physical data |
|---|---|---|---|---|---|---|---|
| 3 | 4-methyl-3-(difluoromethyl)-1-yl-1,2,4-triazol-5(4H)-one | F | CN | $CH_3$ | H | H | m.p.: 153° C. |
| 4 | 6-methyl-2H-pyridazin-3(2H)-one-2-yl | F | CN | $CH_3$ | H | H | m.p.: 159° C. |
| 5 | 1-methyl-2-(difluoromethyl)-4-yl-1,2,4-triazolidine-3,5-dione | F | CN | $CH_3$ | H | H | m.p.: 63° C. |
| 6 | 4-ethyl-3-(difluoromethyl)-1-yl-1,2,4-triazol-5(4H)-one | F | CN | $CH_3$ | H | H | m.p.: 166° C. |
| 7 | 4-methyl-3-(1,1,2,2-tetrafluoroethyl)-1-yl-1,2,4-triazol-5(4H)-one | F | CN | $CH_3$ | H | H | m.p.: 109° C. |
| 8 | 6-methyl-2H-pyridazin-3(2H)-one-2-yl | F | CN | $C_2H_5$ | H | H | logP = 2.07[a] |
| 9 | 5-methyl-2H-pyridazin-3(2H)-one-2-yl | F | CN | $CH_3$ | H | H | logP = 1.07[a] |
| 10 | 4-methyl-5-trifluoromethyl-2H-pyridazin-3(2H)-one-2-yl | F | CN | $CH_3$ | H | H | m.p.: 75° C. |
| 11 | 5-trifluoromethyl-2H-pyridazin-3(2H)-one-2-yl | F | CN | $CH_3$ | H | H | m.p.: 141° C. |

TABLE 1-continued

Examples of the compounds of the formla (I)

| Ex. No. | Z | R¹ | R² | R³ | R⁴ | R⁸ | physical data |
|---|---|---|---|---|---|---|---|
| 12 | (ethyl-N, CF₃, triazolinone) | F | CN | H | H | H | m.p.: 147° C. |
| 13 | (methyl-N, CHF₂-N, triazolidinedione) | F | Cl | CH₃ | H | H | logP = 3.18[a] |
| 14 | (methyl-triazinedione) | F | CN | CH₃ | H | H | m.p.: 80° C. |
| 15 | (methyl-N, CF₃, triazolinone) | F | CN | CH₃ | H | H | m.p.: 57° C. |
| 16 | (methyl/ethyl triazinetrione) | F | Cl | CH₃ | H | H | m.p.: 48° C. |
| 17 | (ethyl-N, CHF₂, triazolinone) | F | CN | CH₃ | H | H | m.p.: 101° C. |
| 18 | (chloro tetrahydroindazole) | F | CN | CH₃ | H | H | logP = 4.22[a] |
| 19 | (phthalimide) | F | CN | CH₃ | H | H | m.p.: 152° C. |
| 20 | (CF₃, Cl, dimethylpyrazole) | F | CN | CH₃ | H | H | logP = 4.11[a] |

TABLE 1-continued

Examples of the compounds of the formla (I)

| Ex. No. | Z | R¹ | R² | R³ | R⁴ | R⁸ | physical data |
|---|---|---|---|---|---|---|---|
| 21 | 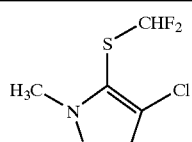 | F | CN | $CH_3$ | H | H | logP = 3.73[a] |
| 22 | 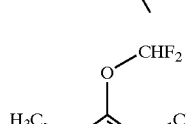 | F | CN | $CH_3$ | H | H | logP = 3.49[a] |

The LogP values given in Table 1 were determined in accordance with EEC directive 79/831 Annex V.A8 by HPLC (High Performance Liquid Chromatography) using a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding data in Table 1 are labelled[a]).

(b) Mobile phases for the determination in the neutral range, 0.01 molar aqueous phosphate buffer solution, acetonitrile; linear gradient from 10% acetonitrile to 90% acetonitrile—the corresponding data in Table 1 are labelled b Calibration was carried out using unbranched alkan-2-ones (with from 3 to 16 carbon atoms) whose logP values are known (determination of the logP values by the retention times using linear interpolation between two successive alkanones).

The lambda-max values were determined in the maxima of the chromatographic signals, using the UV spectra from 200 nm to 400 nm.

Starting Materials of the Formula (II):

Example (II-1)

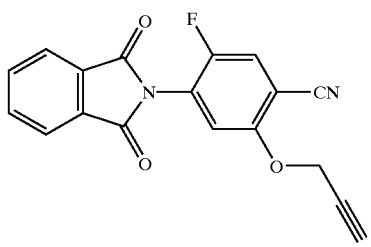

Step 1

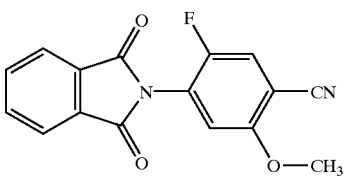

mixture of 8.0 g (50 mmol) of 4-cyano-2-fluoro-5-methoxy-aniline, 7.4 g (50 mmol) of phthalic anhydride and 150 ml of methanol is heated under reflux for 2 days. 0.8 g of 4-dimethylamino-pyridine is then added, and the mixture is heated under reflux for another 24 hours. The mixture is then concentrated, the residue is admixed with water and ethyl acetate and the precipitated product is isolated by filtration with suction and washed with water.

This gives 11.2 g (76% of theory) of N-(2-fluoro-4-cyano-5-methoxy-phenyl)-phthalimide of melting point 245° C. (logP: 2.51).

Step 2

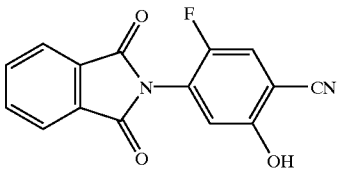

10.6 g (35.8 mmol) of N-(2-fluoro-4-cyano-5-methoxy-phenyl)-phthalimide are initially charged in 300 ml of dichloromethane, and 107 ml (107 mmol) of boron tribromide (1 molar solution in dichloromethane) are added dropwise at from 10° C. to 20° C. The mixture is stirred at 25° C. for 2 days and the admixed with water and stirred for another 10 minutes, and the solid product is isolated by filtration with suction.

This gives 9.2 g (91% of theory) of N-(2-fluoro-4-cyano-5-hydroxy-phenyl)-phthalimide of melting point 247° C. (logP: 2.04).

Step 3

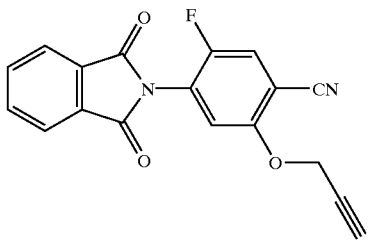

A mixture of 3.0 g (10.6 mmol) of N-(2-fluoro-4-cyano-5-hydroxy-phenyl)-phthalimide, 100 ml of acetonitrile, 1.91 g (13.8 mmol) of potassium carbonate and 1.39 g (1 1.7 mmol) of propargyl bromide is heated under reflux for 18 hours. The mixture is then concentrated, the residue is admixed with ethyl acetate and 2 N hydrochloric acid and the precipitated product is isolated by filtration with suction.

This gives 1.8 g (52.9% of theory) of N-(2-fluoro-4-cyano-5-propargyloxy-phenyl)-phthalimide of melting point 242° C.

Example (II-2))

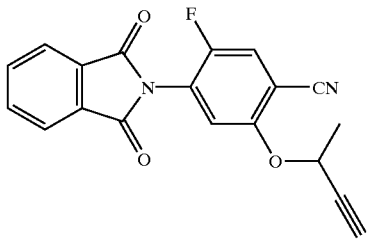

1.0 g (3.55 mmol) of N-(2-fluoro-4-cyano-5-hydroxy-phenyl)-phthalimide are initially charged in 40 ml of tetrahydrofuran with 1.02 g (3.9 mmol) of triphenylphosphine and 0.30 g (4.26 mmol) of but-3-in-2-ol and, with ice cooling (max. 20° C.), 0.70 g (3.9 mmol) of diethyl azodicarboxylate (dissolved in 20 ml of tetrahydrofuran) are added. The mixture is stirred at 25° C. for 24 hours, concentrated and purified on silica gel using cyclohexane/ethyl acetate 2:1.

This gives 0.35 g (29% of theory) of N-[2-fluoro-4-cyano-5-(but-1-in-3-yl)-oxyphenyl]-phthalimide of melting point 170° C. (logP: 2.92).

USE EXAMPLES

Example A

Pre-emergence Test
Solvent: 5 parts by weight of acetone
Emulsifier: 1 part by weight of alkylaryl polyglycol ether
To produce a suitable preparation of active compound, 1 part by weight of active compound is mixed with the stated amount of solvent, the stated amount of emulsifier is added and the concentrate is diluted with water to the desired concentration. Seeds of the test plants are sown in normal soil. After 24 hours, the soil is sprayed with the preparation of active compound such that the particular amount of active compound desired is applied per unit area. The concentration of active compound in the spray liquor is chosen so that the particular amount of active compound desired is applied in 1000 liters of water per hectare.

After three weeks, the degree of damage to the plants is rated in % damage in comparison to the development of the untreated control. The figures denote:

0%=no effect (like untreated control)
100%=total destruction

In this test, for example, the compounds of Preparation Examples 1, 3, 5, 7, 10, 12, 13 and 16 exhibit very strong activity against weeds, and some of them are tolerated well by crop plants, such as, for example, maize, soya and sugar beet.

Example B

Post-emergence Test
Solvent: 5 parts by weight of acetone
Emulsifier: 1 part by weight of alkylaryl polyglycol ether
To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)
100%=total destruction

In this test, for example, the compounds of Preparation Examples 2, 3, 5, 10, 11, 13 and 16 exhibit very strong activity against weeds, and some of them are tolerated well by crop plants, such as, for example, wheat.

What is claimed is:
1. A compound of the Formula (I)

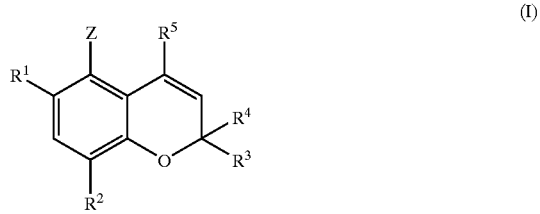

wherein
$R^1$ represents hydrogen, cyano or halogen,
$R^2$ represents cyano, thiocarbamoyl, halogen or represents in each case substituted alkyl or alkoxy,
$R^3$ represents hydrogen, amino, nitro, formyl, carboxyl, cyano, carbamoyl, thiocarbamoyl, halogen, represents hydroxyiminoalkyl or represents in each case optionally substituted alkyl, alkoxy, alkylthio, alkylsulphinyl, alkylsulphonyl, alkylcarbonyl, alkoxycarbonyl, alkylcarbonylamino, alkoxyiminoalkyl, alkenyl, alkenyloxy, alkenylthio, alkinyl, alkinyloxy, alkinylthio, cycloalkyl, cycloalkylalkyl, cycloalkyloxycarbonyl, phenyl or benzyl,
$R^4$ represents hydrogen, halogen or optionally substituted alkyl,
$R^5$ represents hydrogen, halogen or optionally substituted alkyl, and Z represents one of the heterocyclic groupings below

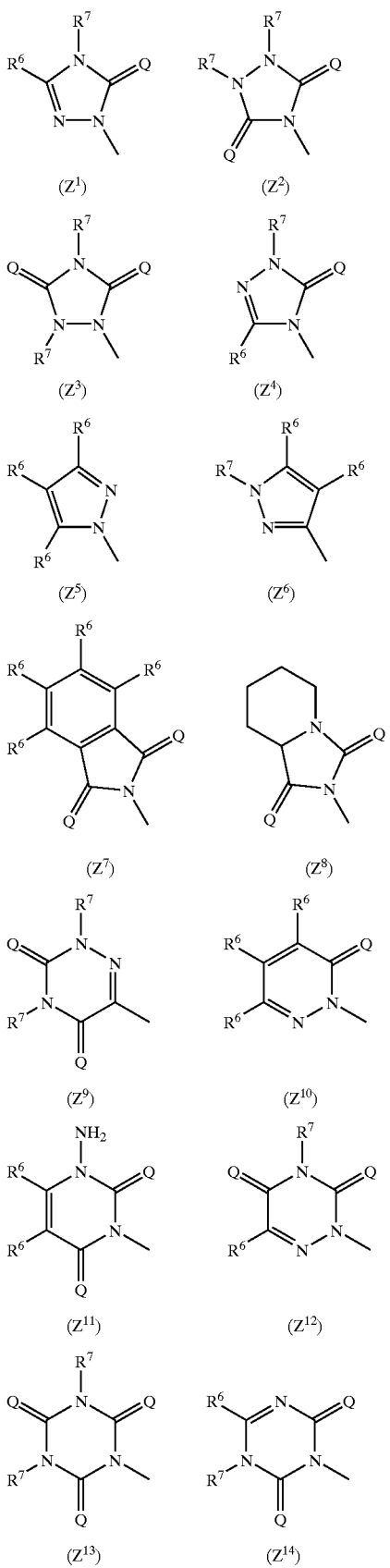

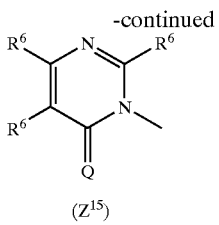

(Z$^{15}$)

wherein
Q represents O or S,
R$^6$ represents hydrogen, amino, nitro, cyano, carboxyl, carbamoyl, thiocarbamoyl, halogen, or represents in each case optionally substituted alkyl, alkoxy, alkylthio, alkylamino, alkoxycarbonyl, dialkylamino, alkenyl, alkenyloxy, alkenylthio, alkinyl, alkinyloxy, alkinylthio, cycloalkyl or cycloalkylalkyl, and
R$^7$ represents hydrogen, hydroxyl, amino, cyano, or represents in each case optionally substituted alkyl, alkoxy, alkoxycarbonyl, alkylamino, alkenyl, alkinyl, cycloalkyl, cycloalkylalkyl, phenyl or phenylalkyl,
wherein optionally two adjacent radicals selected from the pairings consisting of R$^6$ and R$^6$, R$^7$ and R$^7$ and R$^6$ and R$^7$ together represent an alkanediyl or an alkenediyl, each of which said alkanediyl and said alkenediyl respectively comprises a hydrocarbon chain, wherein each of said alkanediyl or said alkenediyl is optionally substituted and wherein each of said substituted or unsubstituted alkanediyl or alkenediyl is optionally interrupted at one or more positions along said hydrocarbon chain by a member selected from the group consisting of O, S, —SO—, SO$_2$—, —NH— and —N(alkyl)—.

2. The compound according to claim 1, wherein
R$^1$ represents hydrogen, cyano, fluorine, chlorine or bromine,
R$^2$ represents cyano, thiocarbamoyl, fluorine, chlorine, bromine, or represents in each case optionally fluorine- and/or chlorine-substituted alkyl or alkoxy having in each case 1 to 4 carbon atoms,
R$^3$ represents hydrogen, amino, nitro, formyl, carboxyl, cyano, carbamoyl, thiocarbamoyl, fluorine, chlorine, bromine, represents hydroxyiminoalkyl having up to 6 carbon atoms, represents in each case optionally cyano-, hydroxyl-, fluorine-, chlorine-, bromine-, C$_1$–C$_4$-alkoxy-, C$_1$–C$_4$-alkylthio-, C$_1$–C$_4$-alkylsulphinyl-, C$_1$–C$_4$-alkylsulphonyl-, C$_1$–C$_4$-alkylsulphonyloxy- or C$_1$–C$_4$-alkylcarbonyloxy-substituted alkyl, alkoxy, alkylthio, alkylsulphinyl or alkylsulphonyl having in each case up to 6 carbon atoms, represents in each case optionally cyano-, fluorine-, chlorine-, bromine- or C$_1$–C$_4$-alkoxy-substituted alkylcarbonyl, alkoxycarbonyl, alkylcarbonylamino or alkoxyiminoalkyl having in each case up to 6 carbon atoms, represents in each case optionally cyano-, fluorine-, chlorine- or bromine-substituted alkenyl, alkenyloxy, alkenylthio, alkinyl, alkinyloxy or alkinylthio having in each case up to 6 carbon atoms, represents in each case optionally cyano-, fluorine-, chlorine-, bromine- or C$_1$–C$_4$-alkyl-substituted cycloalkyl, cycloalkylalkyl or cycloalkyloxycarbonyl having in each case 3 to 6 carbon atoms in the cycloalkyl groups and optionally up to 4 carbon atoms in the alkyl moiety, or represents in each case optionally nitro-, cyano-, fluorine-, chlorine-, bromine-, $C_1$–$C_4$-alkyl- or $C_1$–$C_4$-alkoxy-substituted phenyl or benzyl, $R^4$ represents hydrogen, fluorine, chlorine, bromine, or represents optionally cyano-, fluorine-, chlorine- or $C_1$–$C_4$-alkoxy-substituted alkyl having 1 to 6 carbon atoms, $R^5$ represents hydrogen, fluorine, chlorine, bromine, or represents optionally cyano-, fluorine-, chlorine- or $C_1$–$C_4$-alkoxy-substituted alkyl having 1 to 6 carbon atoms, and Z represents one of the heterocyclic groupings below ($Z^1$) ($Z^2$) ($Z^3$) ($Z^4$) ($Z^5$) ($Z^6$) ($Z^7$) ($Z^8$) ($Z^9$) ($Z^{10}$) ($Z^{11}$) ($Z^{12}$) ($Z^{13}$) ($Z^{14}$) ($Z^{15}$)

wherein

Q represents O or S, $R^6$ represents hydrogen, amino, nitro, cyano, carboxyl, carbamoyl, thiocarbamoyl, halogen, represents in each case optionally cyano-, halogen- or $C_1$–$C_4$-alkoxy-substituted alkyl, alkoxy, alkylthio, alkylamino or alkoxycarbonyl having in each case up to 6 carbon atoms, represents dialkylamino having in each case up to 4 carbon atoms in the alkyl groups, represents in each case optionally cyano- or halogen-substituted alkenyl, alkinyl, alkenyloxy, alkinyloxy, alkenylthio, alkinylthio having in each case up to 6 carbon atoms, or represents in each case optionally cyano-, halogen- or $C_1$–$C_4$-alkyl-substituted cycloalkyl or cycloalkylalkyl having in each case 3 to 6 carbon atoms in the cycloalkyl groups and optionally up to 4 carbon atoms in the alkyl moiety, and $R^7$ represents hydrogen, hydroxyl, amino, cyano, represents in each case optionally cyano-, halogen- or $C_1$–$C_4$-alkoxy-substituted alkyl, alkoxy, alkoxycarbonyl or alkylamino having in each case up to 6 carbon atoms, represents in each case optionally cyano- or halogen-substituted alkenyl or alkinyl having in each case up to 6 carbon atoms, represents in each case optionally cyano-, halogen- or $C_1$–$C_4$-alkyl-substituted cycloalkyl or cycloalkylalkyl having in each case 3 to 6 carbon atoms in the cycloalkyl groups and optionally up to 4 carbon atoms in the alkyl moiety, or represents in each case optionally nitro-, cyano-, halogen-, $C_1$–$C_4$-alkyl- or $C_1$–$C_4$-alkoxy-substituted phenyl, benzyl or phenylethyl, wherein optionally, two adjacent radicals selected from the pairings consisting of $R^6$ and $R^6$, $R^7$ and $R^7$, and $R^6$ and $R^7$ together represent an alkanediyl or an alkenediyl, each of which said alkanediyl and said alkenediyl respectively comprises a hydrocarbon chain having up to 5 carbon atoms, wherein each of said alkanediyl and said alkenediyl respectively are optionally substituted by halogen, and wherein each of said substituted or unsubstituted alkanediyl or alkenediyl is optionally interrupted at one or more positions along said hydrocarbon chain by a member selected from the group consisting of O, S, —SO—, —SO$_2$—, —NH— and —N($C_1$–$C_4$-alkyl)—.

3. The compound according to claim 1, wherein $R^1$ represents hydrogen, fluorine or chlorine, $R^2$ represents cyano, thiocarbamoyl, fluorine, chlorine, bromine, trifluoromethyl, difluoromethoxy or trifluoromethoxy, $R^3$ represents hydrogen, amino, nitro, formyl, carboxyl, cyano, carbamoyl, thiocarbamoyl, fluorine, chlorine, bromine, represents hydroxyiminomethyl, hydroxyiminoethyl or hydroxyiminopropyl, represents in each case optionally cyano-, hydroxyl-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl or ethylsulphonyl, represents in each case optionally cyano-, fluorine-, chlorine-, methoxy- or ethoxy-substituted acetyl, propionyl, n-or i-butyroyl, methoxycarbonyl, ethoxycarbonyl, n- or i-propoxycarbonyl, acetylamino, propionylamino, n- or i-butyroylamino, methoxyiminomethyl, ethoxyiminomethyl, methoxyiminoethyl or ethoxyiminoethyl, represents in each case optionally cyano-, fluorine- or chlorine-substituted propenyl, butenyl, propenyloxy, butenyloxy, propenylthio, butenylthio, propinyl, butinyl, propinyloxy, butinyloxy, propinylthio or butinylthio, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl, cyclohexylmethyl, cyclopropyloxycarbonyl, cyclobutyloxycarbonyl, cyclopentyloxycarbonyl or cyclohexyloxycarbonyl, or represents in each case optionally nitro-, cyano-, fluorine-, chlorine-, bromine-, methyl- or methoxy-substituted phenyl or benzyl, $R^4$ represents hydrogen, fluorine, chlorine, bromine, or represents in each case optionally cyano-, fluorine-, chlorine-, methoxy- or ethoxy-substituted methyl, ethyl, n- or i-propyl, $R^5$ represents hydrogen, fluorine, chlorine, bromine, or represents in each case optionally cyano-, fluorine-, chlorine-, methoxy- or ethoxy-substituted methyl, ethyl, n- or i-propyl, and Z represents one of the heterocyclic groupings below

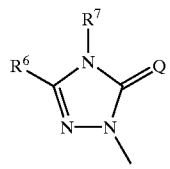

($Z^1$)

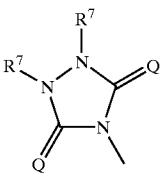

($Z^2$)

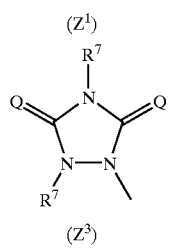

($Z^3$)     ($Z^4$)

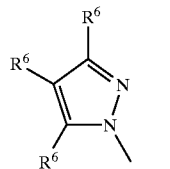

($Z^5$)     ($Z^6$)

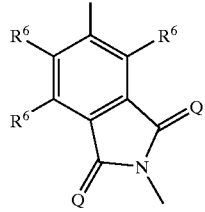

($Z^7$)     ($Z^8$)

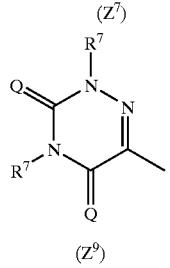

($Z^9$)     ($Z^{10}$)

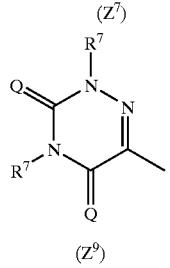

($Z^{11}$)     ($Z^{12}$)

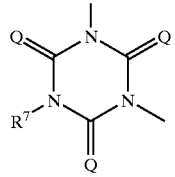 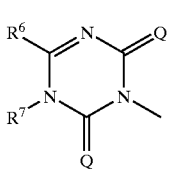

($Z^{13}$)     ($Z^{14}$)

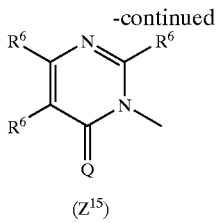

(Z¹⁵)

wherein

Q represents O or S,

R⁶ represents hydrogen, amino, nitro, cyano, carboxyl, carbamoyl, thiocarbamoyl, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino, methoxycarbonyl, ethoxycarbonyl, n- or i-propoxycarbonyl, n-, i-, s- or t-butoxycarbonyl, represents dimethylamino or diethylamino, represents in each case optionally cyano-, fluorine-, chlorine- or bromine-substituted propenyl, butenyl, propinyl, butinyl, propenyloxy, butenyloxy, propinyloxy, butinyloxy, propenylthio, butenylthio, propinylthio or butinylthio, or represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, and R⁷ represents hydrogen, hydroxyl, amino, cyano, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methoxycarbonyl, ethoxycarbonyl, n- or i-propoxycarbonyl, n-, i-, s- or t-butoxycarbonyl, methylamino, ethylamino, n- or i-propylamino, n-, i-, s- or t-butylamino, represents in each case optionally cyano-, fluorine- or chlorine-substituted propenyl, butenyl, propinyl or butinyl, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl- or methoxy-substituted phenyl or benzyl, wherein optionally, two adjacent radicals selected from the pairings consisting of R⁶ and R⁶, R⁷ and R⁷ and R⁶ and R⁷, together represent an alkanediyl or an alkenediyl, each of said alkanediyl and said alkenediyl comprising a hydrocarbon chain, said alkanediyl and said alkenediyl being selected from the group consisting of propane-1,3-diyl (trimethylene), butane-1,4-diyl(tetramethylene), pentane-1,5-diyl(pentamethylene), propene-1,3-diyl, but-1-ene-1,4-diyl and but-2-ene-1,4-diyl, wherein each of said alkanediyl and said alkenediyl is optionally substituted by fluorine or chlorine, and wherein each of said substituted or unsubstituted alkanediyl or alkenediyl is optionally interrupted at one or more positions along said hydrocarbon chain by a member selected from the group consisting of O, S, —SO—, —SO₂—, —NH— and —N(methyl)—.

4. The compound according to claim 1, wherein

R¹ represents hydrogen or fluorine,

R² represents cyano, thiocarbamoyl, chlorine or bromine,

R³ represents hydrogen, carboxyl, cyano, carbamoyl, thiocarbamoyl, fluorine, chlorine, bromine, represents in each case optionally fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl or ethylsulphonyl, represents in each case optionally cyano-, fluorine-, chlorine-, methoxy- or ethoxy-substituted methoxycarbonyl, ethoxycarbonyl, n- or i-propoxycarbonyl, R⁴ represents hydrogen, fluorine, chlorine, bromine, or represents in each case optionally fluorine-, chlorine-, methoxy- or ethoxy-substituted methyl, ethyl, n- or i-propyl, R⁵ represents hydrogen, fluorine, chlorine, bromine, or represents in each case optionally fluorine-, chlorine-, methoxy- or ethoxy-substituted methyl, ethyl, n- or i-propyl, and Z represents one of the heterocyclic groupings below

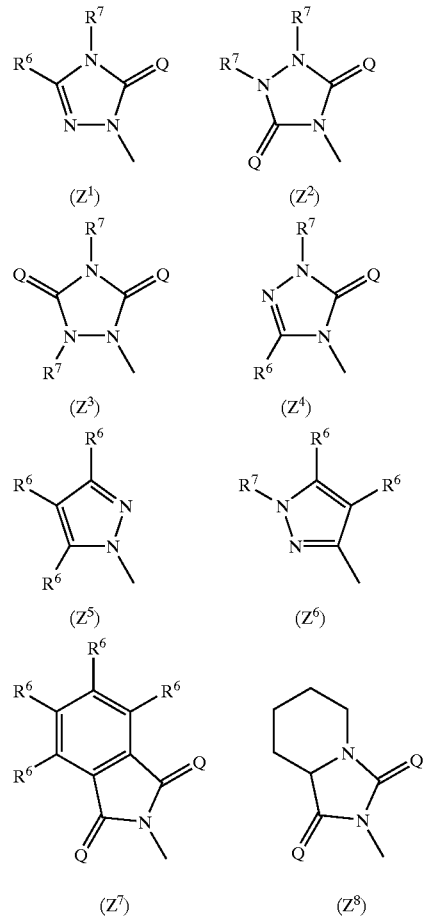

-continued

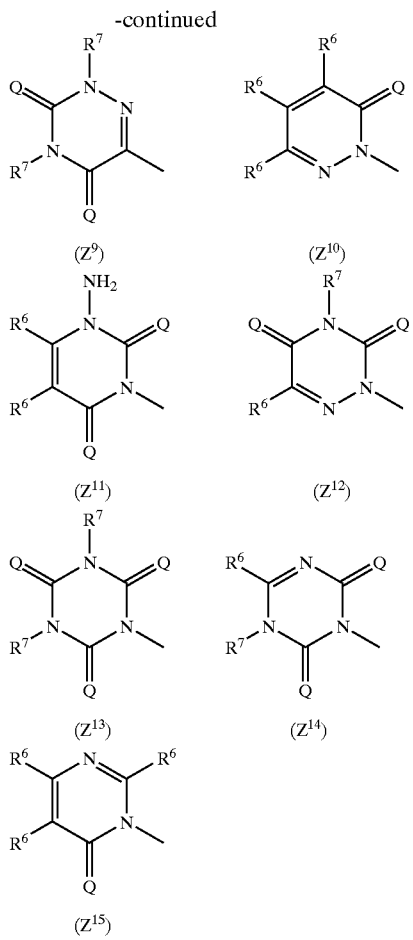

wherein
Q represents O or S,
R⁶ represents hydrogen, fluorine, chlorine, bromine, represents in each case optionally fluorine-, chlorine-, methoxy- or ethoxy-substituted methyl, ethyl, n- or i-propyl, methoxy, ethoxy, n- or i-propoxy, methylamino, ethylamino, n- or i-propylamino, represents dimethylamino, represents in each case optionally cyano-, fluorine-, chlorine- or bromine-substituted propenyl, butenyl, propinyl, butinyl, propenyloxy, butenyloxy, propinyloxy, butinyloxy, propenylthio, butenylthio, propinylthio or butinylthio, and
R⁷ represents hydrogen, represents amino, represents in each case optionally fluorine-, chlorine-, methoxy- or ethoxy-substituted methyl, ethyl, n- or i-propyl, or represents in each case optionally cyano-, fluorine- or chlorine-substituted propenyl, butenyl, propinyl or butinyl,
wherein optionally two adjacent radicals selected from the pairings consisting of R⁶ and R⁶, R⁷ and R⁷ and R⁶ and R⁷ together represent an alkanediyl or an alkenediyl, each of which said alkanediyl and said alkenediyl respectively comprises a hydrocarbon chain, wherein said alkanediyl or said alkenediyl is selected from the group consisting of propane-1,3-diyl(trimethylene), butane-1,4-diyl(tetramethylene), pentane-1,5-diyl (pentamethylene), propene-1,3-diyl, but-1-ene-1,4-diyl or but-2-ene-1,4-diyl, wherein each of said alkanediyl and said alkenediyl is optionally substituted by fluorine or chlorine, and wherein each of said substituted or unsubstituted alkanediyl or alkenediyl is optionally interrupted at one or more positions along said hydrocarbon chain by a member selected from the group consisting of O, S, —SO—, —SO₂—, —NH— and —N(methyl)—.

5. A process for preparing a compound according to any one of claims 1 to 4, comprising the step of:
pyrolysing in the presence of one or more basic nitrogen compounds a
3-alkinyloxy-phenylheterocycle of the Formula (II)

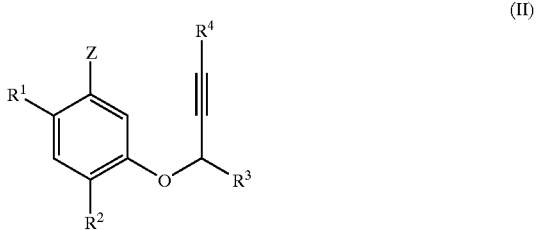

wherein
R¹, R², R³, R⁴ and Z are each as defined in any one of claims 1 to 4.

6. A process for controlling undesirable vegetation, comprising the step of allowing at least one compound according to any one of claims 1 to 4 to act on a member selected from the group consisting of one or more undesirable plants, one or more habitats of said undesirable plants, and combinations thereof.

7. An herbicidal composition comprising a compound according to any one of claims 1 to 4 and a member selected from the group consisting of one or more extenders, one or more surfactants and combinations thereof.

* * * * *